(12) United States Patent
Sargeant et al.

(10) Patent No.: US 8,349,349 B2
(45) Date of Patent: *Jan. 8, 2013

(54) TISSUE ADHESIVES AND SEALANTS AND METHOD FOR THEIR USE

(75) Inventors: Timothy Sargeant, Hamden, CT (US); Joshua Stopek, Guilford, CT (US); Ahmad Robert Hadba, Middlefield, CT (US)

(73) Assignee: Covidien LP, Mansfield, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 12/788,933

(22) Filed: May 27, 2010

(65) Prior Publication Data
US 2010/0285088 A1  Nov. 11, 2010

Related U.S. Application Data

(63) Continuation-in-part of application No. 11/712,333, filed on Feb. 28, 2007, now Pat. No. 7,858,079.

(60) Provisional application No. 60/777,297, filed on Feb. 28, 2006.

(51) Int. Cl.
  *A61K 38/14* (2006.01)
  *A61F 2/00* (2006.01)

(52) U.S. Cl. ........... 424/423; 514/20.9; 525/54.1

(58) Field of Classification Search ........ 424/78.27, 424/423; 525/54.1; 514/20.9
See application file for complete search history.

(56) References Cited

U.S. PATENT DOCUMENTS

| 4,359,049 A | 11/1982 | Redl et al. |
| 4,874,368 A | 10/1989 | Miller et al. |
| 4,978,336 A | 12/1990 | Capozzi et al. |
| 4,979,942 A | 12/1990 | Wolf et al. |
| 5,368,563 A | 11/1994 | Lonneman et al. |
| 6,333,051 B1 | 12/2001 | Kabanov et al. |
| 6,527,749 B1 | 3/2003 | Roby et al. |
| 6,632,929 B1 | 10/2003 | Wilchek et al. |
| 6,638,508 B2 | 10/2003 | Schechter et al. |
| 6,648,922 B2 | 11/2003 | Ung-Chhun et al. |
| 7,858,079 B2 * | 12/2010 | Hadba et al. ......... 424/78.27 |
| 2002/0022266 A1 | 2/2002 | Wagner et al. |
| 2002/0128234 A1 | 9/2002 | Hubbell et al. |
| 2003/0022216 A1 | 1/2003 | Mao et al. |
| 2003/0153001 A1 | 8/2003 | Soane et al. |
| 2003/0181423 A1 | 9/2003 | Clapper et al. |
| 2004/0023413 A1 | 2/2004 | Opalsky |
| 2005/0244453 A1 | 11/2005 | Stucke et al. |
| 2005/0281802 A1 | 12/2005 | Gong et al. |

FOREIGN PATENT DOCUMENTS

| WO | WO 01/06829 | 2/2001 |
| WO | WO 01/06829 A2 | 2/2001 |
| WO | WO 03/000234 | 1/2003 |

OTHER PUBLICATIONS

Xie et al. Design of attachment type of drug delivery system by complex formation of avidin with biotinyl drug model and biotinyl saccharide, QActa Biomaterialia, 1, 2005, pp. 635-641.
Huang et al., Biotin-Derivatized Poly(L-lysine)-g-poly(ethylene glycol): A Novel Polymeric Interface for Bioaffinity Sensing, Langmuir et al., 2002, 18, pp. 220-230.
Salmaso et al. Biochim. Biophys. Acta 1726, 57-66 (2005), available on line May 16, 2005.
Pardridge et al., Pharm. Res. vol. 15, No. 4, 576-582 (1998).
European Search Report for EP 07751965.0-1219 date of completion is Aug. 20, 2012 (11 pages).
Huang et al., "Biotin-Derivatized Poly(L-lysine)-g-poly(ethylene glycol): A Novel Polymeric Interface for Bioaffinity Sensing", Langmuir et al., 2002, 18, pp. 220-230.

* cited by examiner

*Primary Examiner* — Chih-Min Kam

(57) ABSTRACT

Compositions provided by mixing a biotin-containing component and an avidin-containing component are useful as an adhesive or sealant for medical/surgical uses.

14 Claims, No Drawings

TISSUE ADHESIVES AND SEALANTS AND METHOD FOR THEIR USE

CROSS-REFERENCE TO RELATED APPLICATIONS

This application is a continuation-in-part of U.S. patent application Ser. No. 11/712,333 filed Feb. 28, 2007, now U.S. Pat. No. 7,858,079, which claims priority to, and the benefit of, U.S. Provisional Patent Application No. 60/777,297 filed Feb. 28, 2006, the entire disclosures of each of which are incorporated by reference herein.

TECHNICAL FIELD

The present disclosure relates to compositions containing macromers capable of forming a matrix and the use of compositions containing these macromers as surgical adhesives or sealants.

DESCRIPTION OF RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, preferably a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, cyanoacrylate adhesives can have a high flexural modulus which can limit their usefulness. Another type of tissue sealant that is currently available utilizes components derived from bovine and/or human sources. For example, fibrin sealants are available. However, as with any natural material, variability in the material is frequently observed.

It would be desirable to provide a biological adhesive and/or sealant that is fully synthetic and therefore highly consistent in its properties without the concern of viral transmission. Such a composition should be flexible and biocompatible and should be suitable for use as an adhesive or sealant.

SUMMARY

Compositions containing both a biotin-containing component and an avidin-containing component are useful as adhesives and/or sealants in medical or surgical applications. A biocompatible composition of the present disclosure may include an implant including a substrate; a first component including a tissue binding end group and a functional group such as biotin and avidin; and a second component including a substrate binding end group and a functional group such as biotin and avidin, wherein the functional group of the first component is different than the functional group of the second component, and one of the first and second components adheres to a tissue surface and the other of the first and second components adheres to the implant.

In embodiments, the implant is a tissue engineered construct. The tissue engineered construct may be a foam, film, tissue scaffold, pledget, buttress, or mesh.

In embodiments, the tissue binding end group of the first component and/or the substrate binding end group of the second component may be the functional groups of a macromolecule. In other embodiments, the tissue binding end group of the first component and/or the substrate binding end group of the second component may be covalently bound to a macromolecule. In yet other embodiments, the tissue binding end group of the first component and/or the substrate binding end group of the second component may be conjugated to a macromolecule through the use of a linking agent.

In embodiments, the biotin and/or avidin functional groups may be covalently bound to a macromolecule, and in other embodiments the biotin and/or avidin functional groups may be conjugated to a macromolecule through the use of a linking agent.

Methods of adhering an implant to tissue are also disclosed. In embodiments, a method for adhering an implant to tissue includes applying a first component including a tissue binding end group and a functional group such as biotin and avidin to a tissue surface; applying a second component including a substrate binding end group and a functional group such as biotin and avidin to an implant comprising a substrate, wherein the functional group of the first component is different than the functional group of the second component; and contacting the tissue surface with the implant to adhere the implant to the tissue via avidin-biotin affinity binding.

DETAILED DESCRIPTION

The present disclosure relates to a composition for use as a tissue adhesive or sealant, which is biocompatible and non-immunogenic. The composition can be employed to adhere tissue edges, seal air/fluid leaks in tissues, adhere medical devices to tissue and for tissue augmentation such as sealing or filling voids or defects in tissue. The composition can be applied to living tissue and/or flesh of animals, including humans.

While certain distinctions may be drawn between the usage of the terms "flesh" and "tissue" within the scientific community, the terms are used interchangeably herein as referring to a general substrate upon which those skilled in the art would understand the present adhesive to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic or ascite tissue.

The composition of the present disclosure includes a component having at least one biotin group, or a derivative thereof, and a component having at least one avidin group, or a derivative thereof. The biotin moiety on the one component and the avidin group on the other component bond to one another thereby providing the present compositions. When the two components are combined, the composition rapidly forms a three dimensional gel-like adhesive matrix. The composition may, in embodiments, be utilized as an adhesive or sealant. The composition can also act as a drug carrier, allowing controlled release and direct delivery of a drug to a specific location in an animal, especially a human. Each component is preferably synthetic to reduce or eliminate immunoreactions in a subject's tissue.

Biotin (also known as vitamin H, coenzyme R) is a readily water-soluble substance found at low concentrations in blood and tissues. Biotin acts as a carrier of activated $CO_2$ and permits the transfer of $CO_2$ to acceptors without the need for additional free energy. Activated carboxybiotin is usually attached to an enzyme that is required for the formation of carboxybiotin. For example, biotin may be attached to pyruvate carboxylase which, in the presence of acetyl CoA, catalyzes the formation of carboxybiotin and the subsequent transfer of the activated carboxyl group to pyruvate, to form oxaloacetate.

The biotin-containing component can be any biocompatible compound that includes one or more biotin moieties. The compound can be any small molecule or polymer capable of being functionalized. The biotin-containing component can be bioabsorbable or non-bioabsorbable. In some embodiments, the biotin-containing component may be derived from a polysaccharide. Suitable polysaccharides include, for example, sorbitol, mannitol, sucrose, dextran, cyclodextrin, combinations thereof, and the like. In other embodiments, the biotin-containing component may be derived from a polyalkylene oxide ("PAO"). Suitable PAOs include, but are not limited to, polyethylene glycol ("PEG"), polyethylene oxide ("PEO"), polypropylene oxide ("PPO"), a polyethylene glycol with lactide linkages, polypropylene glycol ("PPG"), copolyethylene oxide lock or random copolymers, and poloxamers such as polyethylene oxide (PEO) copolymers with polypropylene oxide (PPO) such as the triblock PEO-PPO copolymers commercially available as PLURONICS® from BASF Corporation (Mt. Olive, N.J.). Various forms of PAOs, including functionalized PEGs, are also commercially available from providers which include, for example, Shearwater Polymers, Inc., Huntsville, Ala., and Texaco Chemical Company, Houston, Tex. In embodiments, combinations of the foregoing PAOs may be utilized.

In some embodiments, the biotin-containing component includes a bioabsorbable polymer. A bioabsorbable polymer breaks down in the body and may be gradually absorbed or eliminated by the body by hydrolysis, metabolic processes, or bulk or surface erosion. Examples of bioabsorbable materials suitable for making the biotin-containing component include, but are not limited to, polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, polyamino acids (including, but not limited to, polyglutamic acid, polyaspartic acid, and synthetic amino acids with pendant acidic groups, including those commercially available from Sigma-Aldrich (St. Louis, Mo.), absorbable cyanoacrylates, poly(trimethylene carbonate), poly(iminocarbonate), copoly(ether-esters), polyalkylene oxalates, polyphosphazenes, polyiminocarbonates, and aliphatic polycarbonates. In some embodiments, combinations of the foregoing bioabsorbable materials may be utilized. For example, one or more of the foregoing absorbable polymers can be reacted with a PAO to provide a degradable polymer having hydrophilic properties which then can be functionalized with biotin to provide the biotin-containing component.

In some embodiments the biotin-containing component may be modified to produce a multi-functional material, i.e., one having a branched or star configuration. Methods for achieving branching are within the purview of those skilled in the art and include, for example, reacting the compound used to form the biotin-containing component with a multifunctional branching agent either prior to or after functionalization with biotin. Suitable multifunctional branching agents include, but are not limited to, tris(hydroxymethyl)aminomethane (also known as 2-amino-2-(hydroxymethyl)-1,3-propanediol), enterodiol, cyclodextrins, polysaccharides (e.g., sorbitols, mannitols, sucrose, dextrans, cyclodextrins, etc.) polyols, polyvinyl alcohols, combinations thereof, and the like.

In embodiments, the molecular weight of the biotin-containing component may be from about 200 to about 50,000, and in embodiments from about 500 to about 5,000.

Polymers and other compounds (e.g., small molecules) can be functionalized with biotin, i.e., biotinylated, according to any method within the purview of those skilled in the art. For example, PEG can be functionalized using those methods disclosed in Chapter 22 of Poly(ethylene Glycol) Chemistry: Biotechnical and Biomedical Applications, J. Milton Harris, ed., Plenum Press, NY (1992).

In embodiments, the biotin-containing component includes a three part molecule containing a macromolecule or polymer, a tissue or substrate binding end group, and a biotinylated end group. The macromolecule may include both natural and synthetic biodegradable materials, as well as combinations thereof.

Representative natural biodegradable macromolecules include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups include, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein, and copolymers and blends thereof; alone or in combination with synthetic polymers.

Representative synthetic biodegradable macromolecules which may be utilized include polyhydroxy acids prepared from lactone monomers such as glycolide, lactide, caprolactone, ϵ-caprolactone, valerolactone, and δ-valerolactone; carbonates (e.g., trimethylene carbonate, tetramethylene carbonate, and the like); dioxanones (e.g., 1,4-dioxanone and p-dioxanone); 1,dioxepanones (e.g., 1,4-dioxepan-2-one and 1,5-dioxepan-2-one); and combinations thereof. Polymers formed therefrom include: polylactides; poly(lactic acid); polyglycolides; poly(glycolic acid); poly(trimethylene carbonate); poly(dioxanone); poly(hydroxybutyric acid); poly (hydroxyvaleric acid); poly(lactic-co-glycolic acid); poly (lactide-co-(ϵ-caprolactone-)); poly(glycolide-co-(ϵ-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; polyortho esters; and copolymers, block copolymers, homopolymers, blends, and combinations thereof.

The macromolecules may be functionalized to provide reactive sites to attach the tissue or substrate binding end group, and/or the biotinylated end group. For example, amines may be provided on proteins, aminoglycans (such as chitosan, chondrotins, hyaluronic acid, and heparin), and polypeptides (like polylysine); carboxyl groups may be provided on proteins, polypeptides (like poly(glutamic acid)), polysaccharides (such as carboxylated dextran and carboxymethyl cellulose), and synthetic polymers (like carboxylated PEG and PEG-diadipate); hydroxyl groups may be provided on polysaccharides (like dextran), di-PEG adipate, and aliphatic polyesters (such as poly(lactic acid), poly(glycolic acid), poly(caprolactone), poly(trimethylene carbonate, poly (P-Dioxanone), and copolymers thereof); and thiols may be provided on some proteins. Alternatively, the macromolecules may be functionalized with tissue or substrate binding end groups, such as poly(lactic acid) and/or poly(glycolic acid), which include terminal carboxyl or hydroxyl groups.

In embodiments, the tissue or substrate binding end group, and/or the biotinylated reactive end group may be conjugated to the macromolecule through the use of a linking agent. For amine containing macromolecules, for example, isothiocyanates, isocyanates, acyl azides, N-hydroxysuccinimide (NHS) and sulfo-NHS esters, sulfonyl chlorides, aldehydes and glyoxals, epoxides and oxiranes, carbonates, arylating agents, imidoesters, carbodiimides, and anhydrides may be utilized. For carboxyl containing macromolecules, for example, diazoalkanes and diazoacetyl compounds may be utilized, as well as carbonyldiimidazoles, carbodiimides, and NHS, which convert carboxylic acid into a reactive intermediate which is susceptible to reaction with amines or alcohols. For hydroxyl containing macromolecules, for example, epoxides and oxiranes, acyl azides, carbonyldiimidazole, disuccinimidyl carbonate and hydroxysuccinimidyl chloroformate, alkyl halogens, isocyanates, and methacryloyl or acryloyl chloride may be utilized, as well as oxidation with periodate and enzymatic oxidation.

In some embodiments, the tissue or substrate binding end groups may be conjugated to the macromolecule via succinimidyl esters such as NHS and sulfo-NHS; isocyanates and isothiocyanates; aldehydes such as oxidized starch, oxidized dextran, and oxidized PEG; and by Michael's Addition of acrylates which react with thiol groups.

Biotin is commercially available with different functional groups, such as amine, sulfhydryl, carbonyl, and carboxy reactive chemistries. It is envisioned that a suitable commercially available functionalized biotin may be chosen based upon the macromolecule to which it is to be bound.

The avidin-containing component can be any biocompatible compound that has been functionalized with avidin, streptavidin or their derivatives. Thus, as used herein, an avidin-containing component can include one or more moieties derived from avidin, streptavidin or their derivatives. The compound can be any small molecule or a polymer capable of being functionalized. The avidin-containing component can be bioabsorbable or non-bioabsorbable.

Avidin (a glycoprotein from chicken egg white) and streptavidin (from *Streptomyces avidinii*) are two related proteins that bind biotin with similar dissociation constants of about $10^{-15}$ M. Avidin occurs naturally in a tetrameric form with four identical subunits, each having about 128 amino acid residues, six mannose residues, and three glucosamine residues, for a combined molecular weight of approximately 68,000. In addition to the ability of avidin and streptavidin to bind biotin, many of their physical properties are quite similar. Both, for example, are constructed of four non-covalently attached identical subunits, each of which bears a single biotin-binding site. The subunit Mr values are very similar. Moreover, several short stretches in the sequences of the two proteins are preserved, particularly two Trp-Lys stretches that occur at approximately similar positions.

Avidin, streptavidin and their derivatives, as well as methods for obtaining the same, are within the purview of those skilled in the art. For example, modified avidins have been prepared, such as N-acyl avidins, e.g., N-formyl, N-acetyl and N-succinyl avidins. These derivatives of avidin reduce the charge of the protein, but they may all be prepared via covalent attachment to the available lysines of avidin. An alternative to lysine modification is the modification of arginines on avidin. In this case, the lysines are still available for subsequent interaction. Two different derivatives of avidin which are modified in this manner are commercially available. One, ExtrAvidin®, can be obtained in various functionally derivatized or conjugated forms from Sigma Chemical Company (St. Louis, Mo.). A second, NeutraLite Avidin™ (a product of Belovo Chemicals, Bastogne, Belgium), is a deglycosylated form of avidin obtained enzymatically, which exhibits a neutral pH and bears free lysine groups for further derivatization. Other avidin derivatives include those disclosed in U.S. Pat. Nos. 6,638,508 and 6,632,929, the entire disclosures of each of which are incorporated by reference herein.

In some embodiments, the avidin-containing component may be derived from a polysaccharide. Suitable polysaccharides include, for example, sorbitol, mannitol, sucrose, dextran, cyclodextrin, and the like, and combinations thereof. In other embodiments, the avidin-containing component may be derived from a polyalkylene oxide ("PAO"). Suitable PAOs include, but are not limited to, polyethylene glycol ("PEG"), polyethylene oxide ("PEO"), polypropylene oxide ("PPO"), a polyethylene glycol with lactide linkages, polypropylene glycol ("PPG"), co-polyethylene oxide lock or random copolymers, and poloxamers such as polyethylene oxide (PEO) copolymers with polypropylene oxide (PPO) such as the triblock PEO-PPO copolymers commercially available as PLURONICS® from BASF Corporation (Mt. Olive, N.J.). Various forms of PAOs, including functionalized PEGs, are also commercially available from providers which include, for example, Shearwater Polymers, Inc., Huntsville, Ala., and Texaco Chemical Company, Houston, Tex. In embodiments, combinations of the foregoing PAOs may be utilized.

In some embodiments, a bioabsorbable polymer is used to prepare the avidin-containing component. A bioabsorbable polymer breaks down in the body and may be gradually absorbed or eliminated by the body by hydrolysis, metabolic processes, or bulk or surface erosion. Examples of bioabsorbable materials suitable for making the avidin-containing component include, but are not limited to, polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, polyamino acids (including, but not limited to, polyglutamic acid, polyaspartic acid, and synthetic amino acids with pendant acidic groups, including those commercially available from Sigma-Aldrich (St. Louis, Mo.), absorbable cyanoacrylates, poly(trimethylene carbonate), poly(iminocarbonate), copoly(ether-esters), polyalkylene oxalates, polyphosphazenes, polyiminocarbonates, and aliphatic polycarbonates. In some embodiments, combinations of the foregoing bioabsorbable materials may be utilized. For example, one or more of the foregoing absorbable polymers can be reacted with a PAO to provide a degradable polymer having hydrophilic properties which then can be functionalized with avidin to provide the avidin-containing component.

In some embodiments the avidin-containing component may be modified to produce a multi-functional material, i.e., one having a branched or star configuration. Methods for achieving branching are within the purview of those skilled in the art and include, for example, reacting the compound used to form the avidin-containing component with a multifunctional branching agent either prior to or after functionalization with avidin. Suitable multifunctional branching agents include, but are not limited to, tris(hydroxymethyl)aminomethane (also known as 2-amino-2-(hydroxymethyl)-1,3-propanediol), enterodiol, polysaccharides (e.g., sorbitols, mannitols, sucrose, dextrans, cyclodextrins, etc.) polyols, polyvinyl alcohols, combinations thereof, and the like.

In embodiments, the molecular weight of the avidin-containing component may be from about 200 to about 50,000, and in embodiments from about 500 to about 5,000.

Polymers and other compounds (e.g., small molecules) can be functionalized with avidin using any method within the purview of those skilled in the art. For example, PEG can be functionalized using those methods disclosed in Chapter 22 of Poly(ethylene Glycol) Chemistry: Biotechnical and Biomedical Applications, J. Milton Harris, ed., Plenum Press, NY (1992).

In embodiments, the avidin-containing component includes a three part molecule containing a macromolecule or polymer, a tissue or substrate binding end group, and an avidinylated end group. The macromolecule may include both natural and synthetic biodegradable materials, as well as combinations thereof, which may include or may be functionalized with tissue or substrate binding reactive groups as described above.

Avidin is a protein which includes free amines and carboxyl groups for reaction. It is envisioned that a suitable functionalized macromolecule may be employed for binding to the amine or carboxyl groups of avidin.

Each avidin or streptavidin binds one molecule of biotin. The unique feature of this binding is the strength and specificity of formation of the avidin-biotin complex. The resultant affinity constant, estimated at $1.6 \times 10^{15} M^{-1}$ for avidin and $2.5 \times 10^{13} M^{-1}$ for streptavidin, is the highest known for a protein and an organic ligand. It is so strong that biotin cannot be released from the binding site, even when subjected to a variety of drastic conditions such as high concentrations of denaturing agents at room temperature, e.g., 6 M guanidinium hydrochloride, 3 M guanidinium thiocyanate, 8 M urea, 10% β-mercaptoethanol or 10% sodium dodecyl sulfate. Under combined treatment with guanidinium hydrochloride at low pH (1.5) or upon heating (>70° C.) in the presence of denaturing agents or detergents, the protein may be denatured, and biotin can be dislodged from the disrupted binding site.

The biotin-containing component and the avidin-containing component may be prepared and stored separately prior to use. The biotin-containing component and/or the avidin-containing component can be stored neat. Alternatively, the biotin-containing component and/or the avidin-containing component can be stored as a dry powder that may be reconstituted (e.g., by mixing with water or other biocompatible solvent) immediately prior to use. Alternatively, the biotin-containing component and/or the avidin-containing component can be formulated into compositions containing water or some other biocompatible solvent and stored separately until application. For example, these formulations can be solutions, emulsions, and dispersions. The concentrations of the biotin-containing component and the avidin-containing component in such formulations will vary depending upon a number of factors, including the types and molecular weights of the particular polymers used and the desired end use application, i.e., as an adhesive or sealant. In embodiments, the biotin-containing component and/or the avidin-containing component may be present in such formulations in amounts from about 5% to about 95% by weight of the composition, in embodiments from about 20% to about 80% by weight of the composition.

In some embodiments, the present compositions may contain one or more bioactive agents. The bioactive agent may be included within the formulation containing the biotin-containing component, the avidin-containing component, or both. Alternatively, the bioactive agent can be mixed with the biotin-containing component and/or the avidin-containing component immediately prior to use. The term "bioactive agent", as used herein, is used in its broadest sense and includes any substance or mixture of substances that may have clinical use. Consequently, bioactive agents may or may not have pharmacological activity per se, e.g., a dye. Alternatively a bioactive agent could be any agent which provides a therapeutic or prophylactic effect, a compound that affects or participates in tissue growth, cell growth or cell differentiation, a compound that may be able to invoke a biological action such as an immune response, or could play any other role in one or more biological processes.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used in the present compositions.

Suitable antimicrobial agents which may be included as a bioactive agent in the compositions of the present disclosure include triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent in the compositions of the present disclosure.

Other bioactive agents which may be included as a bioactive agent in the compositions of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs;

estrogens; antibacterials; antibiotics; anti-fungals; anti-virals; anticoagulants; anticonvulsants; antidepressants; antihistamines; and immunological agents.

Other examples of suitable bioactive agents which may be included in the composition of the present disclosure include viruses and cells; peptides; polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; and protein agonists; nucleic acids such as antisense molecules, DNA, and RNA; oligonucleotides; and ribozymes; naturally occurring polymers, including proteins such as collagen and derivatives of various naturally occurring polysaccharides such as glycosaminoglycans; peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the composition of the present disclosure. Methods for incorporating enzymes into liposomes and/or microspheres are within the purview of those skilled in the art.

A single bioactive agent may be utilized in the present compositions or, in alternate embodiments, any combination of bioactive agents may be utilized.

A variety of optional ingredients may also be added to the compositions of the present disclosure. A phospholipid surfactant that provides antibacterial stabilizing properties and helps dispense other materials in the compositions may be added to the compositions of the present disclosure. Imaging agents such as iodine or barium sulfate, or fluorine, can also be combined with the compositions of the present disclosure to allow visualization of the surgical area through the use of imaging equipment, including X-ray, MRI, and CAT scan.

Once obtained, the biotin-containing component and the avidin-containing component can be combined to form compositions of the present disclosure which, in embodiments, may be utilized as a biocompatible adhesive or sealant. In embodiments, the biotin-containing component and the avidin-containing component may be applied directly onto a tissue surface to form a three-dimensional crosslinked matrix as a result of the reaction between the biotin groups with the avidin groups.

Application of the present compositions, with or without other additives, can be done by any conventional means. These include dripping, brushing, or other direct manipulation of the composition on the tissue surface, or spraying of the biocompatible composition to the surface. In open surgery, application by hand, forceps, or the like is contemplated. In endoscopic surgery, the biocompatible composition can be delivered through the cannula of a trocar, and spread at the site by any device within the purview of those skilled in the art.

The biocompatible composition can also be dispensed from a conventional adhesive dispenser, which may provide mixing of the biotin-containing component and the avidin-containing component prior to dispensing. Such dispensers are disclosed, for example, in U.S. Pat. Nos. 4,978,336; 4,361,055; 4,979,942; 4,359,049; 4,874,368; 5,368,563; and 6,527,749, the entire disclosures of each of which are incorporated herein by reference. Thus, in embodiments, the present disclosure also relates to an apparatus that includes a first chamber containing a first composition containing a biotin-containing component, a second chamber containing a second composition containing an avidin-containing component, and one or more outlets for simultaneously dispensing the first and second compositions.

The biocompatible composition resulting from the mixture of the biotin-containing component and the avidin-containing component can be used in human and animal medical applications including, but not limited to, wound closure (including surgical incisions and other wounds), adhesives for medical devices (including implants), sealants and void fillers, and embolic agents. The biocompatible compositions can be used in a medical/surgical capacity in place of, or in combination with, sutures, staples, clamps and the like. Use of the present compositions can eliminate or substantially reduce the number of sutures normally required during current practices, and eliminate the subsequent need for removal of staples and certain types of sutures and thus can be particularly useful for use with delicate tissues where sutures, clamps or other conventional tissue closure mechanisms may cause further tissue damage.

In some embodiments, the biocompatible composition can be used to seal or adhere delicate tissue together, such as lung tissue, in place of conventional tools that may cause mechanical stress.

Additional applications of the biocompatible composition include sealing tissues to prevent or control blood, or other fluid leaks, at suture or staple lines. In another embodiment, the biocompatible composition can be used to attach skin grafts and position tissue flaps during reconstructive surgery. In still another embodiment, the biocompatible composition can be used to close tissue flaps in periodontal surgery. The resulting biocompatible composition can also be used to seal air and/or fluid leaks in tissue as well as to prevent post-surgical adhesions and to fill voids and/or defects in tissue. Alternatively, the present compositions can be cured into useful solid shapes such as, for example, anti-adhesion barriers, staple buttresses, suture pledgets, tissue bulking devices, and the like. The present compositions can also be applied as a biocompatible coating to any desired medical device.

To effectuate the joining of two tissue edges, the two edges are approximated, the biotin-containing component is combined with the avidin-containing component and applied to the approximated edges, and the two components crosslink with each other thereby forming the biocompatible composition of the present disclosure. In other embodiments, the biotin-containing component may be applied to one tissue edge, the avidin-containing component may be applied to a second tissue edge, and the two tissue edges approximated so that the biotin-containing component is combined with the avidin-containing component, and the two components crosslink with each other thereby forming the biocompatible composition of the present disclosure. The crosslinking reaction is rapid, generally taking less than one minute. In this case the composition of the present disclosure can be used as an adhesive to close a wound, including a surgical incision. In such a case, the composition of the present disclosure can be applied to the wound and allowed to set, thereby closing the wound.

In another embodiment, the biocompatible composition of the present disclosure may be used to adhere a medical device to tissue, rather than secure two edges of tissue. In some cases the medical device may include a coating of the biotin-containing component, the avidin-containing component, or both. In some aspects, the medical device includes an implant. Other medical devices include, but are not limited to, pacemakers, stents, shunts and the like. In embodiments, for adhering a device to the surface of animal tissue, the composition of the present disclosure, or the individual components thereof, can be applied to the device, the tissue surface or both. The device, biocompatible composition (or components thereof), and tissue surface are then brought into contact with each other and the composition is allowed to set, thereby adhering the device and surface to each other.

In other embodiments, one of the biotin-containing or avidin-containing components may be bound to an implant, such as a tissue engineered construct (e.g., foams, films, tissue scaffolds, pledgets, buttresses, and meshes), and the other component may be applied and bound to a tissue surface, thus providing the implant and tissue surface with a biotin or avidin rich surface. For example, a first precursor possessing tissue reactive groups could be applied to tissue and allowed to bind thereto, thus creating an avidin or biotin rich surface. An implant, having avidin when the first precursor has biotin, or having biotin when the first precursor has avidin, may then be placed in contact with the tissue, whereby the avidin-biotin affinity acts to adhere the implant to the tissue.

In embodiments, a collagen-based scaffold may be chemically reacted with the free amines of an avidin-containing component to covalently bind the avidin to the surface of the scaffold. The biotin-containing component may be bound to a tissue surface via tissue binding reactive groups, such as amine, carboxyl, or hydroxyl groups. The biotin may be directly conjugated to this reactive group or it may be attached by a linking agent as described above.

The implant may be placed in contact with of the tissue surface and the biotin-avidin affinity acts to adhere the implant to the tissue. As the binding is non-covalent, the implant may be removed and re-attached if not successfully positioned upon first contact, while still providing good tissue healing upon proper placement.

In another embodiment, in the case of cartilage repair, a hydroxy-reactive tissue binding end group may be linked to avidin to coat and adhere to subchondral bone. A biotinylated tissue scaffold could then be attached to the subchondral bone and affixed firmly in place, thereby preventing detachment by high loads and shear experienced in the joint.

In the case of breast reconstruction, an amine-reactive tissue binding end group may be linked to avidin to coat and adhere to an underlying tissue surface and to a skin flap. A biotinylated tissue scaffold (or mesh) may be positioned between to the underlying tissue surface and the skin flap such that the tissue scaffold (or mesh) acts like double-sided tape to adhere the underlying tissue and the skin flap, while also fostering tissue ingrowth and healing. In embodiments, the tissue scaffold may also be used for local delivery of pain medications, thereby also providing pain relief from the scaffold.

The present biocompatible composition can also be used to prevent post surgical adhesions. In such an application, the biocompatible composition may be applied and cured as a layer on surfaces of internal tissues in order to prevent the formation of adhesions at a surgical site during the healing process.

When used as a sealant, the biocompatible composition of the present disclosure can be used in surgery to prevent or inhibit bleeding or fluid leakage both during and after a surgical procedure. It can also be applied to prevent air leaks associated with pulmonary surgery. The biocompatible composition can be applied directly to the desired area in at least an amount necessary to seal off any defect in the tissue and seal off any fluid or air movement.

The present biocompatible composition has a number of advantageous properties. The resulting biocompatible compositions of the present disclosure are safe and biocompatible, possess enhanced adherence to tissue, are biodegradable, have enhanced hemostatic potential, have low cost, and are easy to prepare and use. By varying the selection of the polymer components, the strength and elasticity of the biocompatible composition can be controlled, as can the gelation time.

The biocompatible composition rapidly forms a compliant gel matrix, which ensures stationary positioning of tissue edges or implanted medical devices in the desired location and lowers overall required surgical/application time. The biocompatible composition exhibits little or no swelling upon gel matrix formation, and therefore retains the positional integrity of the aligned tissue edges and/or location of a medical device. The biocompatible composition forms strong cohesive bonds, based in part on the high affinity of biotin for avidin and/or streptavidin. It exhibits excellent mechanical performance and strength, while retaining the necessary pliability to adhere living tissue. This strength and pliability allows a degree of movement of tissue without shifting the surgical tissue edge. Additionally, the biocompatible composition is biodegradable, allowing the degradation components to pass safely through the subject's body.

It will be understood that various modifications may be made to the embodiments disclosed herein. Therefore the above description should not be construed as limiting, but merely as exemplifications of embodiments of the present disclosure. Those skilled in the art will envision other modifications within the scope and spirit of the claims appended hereto.

What is claimed is:

1. A biocompatible composition comprising:
   an implant comprising a substrate;
   a first component comprising a biodegradable material including a tissue binding end group and a functional group selected from the group consisting of biotin and avidin; and
   a second component comprising a biodegradable material including a substrate binding end group and a functional group selected from the group consisting of biotin and avidin,
   wherein the biodegradable material of the first component, the second component, or both, is selected from the group consisting of polylactides, poly(lactic acid), polyglycolides, poly(glycolic acid), poly(trimethylene carbonate), poly(dioxanone), poly(hydroxybutyric acid), poly(hydroxyvaleric acid), poly(lactic-co-glycolic acid), poly(lactide-co-(ε-caprolactone-)), poly(glycolide-co-(ε-caprolactone)), polycarbonates, poly(pseudo amino acids), poly(amino acids), poly(hydroxyalkanoate)s, polyalkylene oxalates, polyoxaesters, polyanhydrides, polyester anyhydrides, polyortho esters, and copolymers, block copolymers, homopolymers, blends, and combinations thereof, and wherein the functional group of the first component is different than the functional group of the second component and the first component adheres to a tissue surface and the second component adheres to the implant.

2. The biocompatible composition according to claim 1, wherein the implant is a tissue engineered construct.

3. The biocompatible composition according to claim 2, wherein the tissue engineered construct is selected from the group consisting of foams, films, tissue scaffolds, pledgets, buttresses, and meshes.

4. The biocompatible composition according to claim 1, wherein the tissue binding end group of the first component is a functional group of a macromolecule.

5. The biocompatible composition according to claim 1, wherein the substrate binding end group of the second component is a functional group of a macromolecule.

6. The biocompatible composition according to claim 1, wherein at least one of the tissue binding end group and the functional group of the first component is covalently bound to a macromolecule.

7. The biocompatible composition according to claim 1, wherein at least one of the substrate binding end group and the functional group of the second component is covalently bound to a macromolecule.

8. The biocompatible composition according to claim 1, wherein at least one of the tissue binding end group and the functional group of the first component is conjugated to a macromolecule through a linking agent.

9. The biocompatible composition according to claim 1, wherein at least one of the substrate binding end group and the functional group of the second component is conjugated to a macromolecule through a linking agent.

10. The biocompatible composition according to claim 1, further comprising a bioactive agent.

11. The biocompatible composition according to claim 1, wherein the tissue binding end group and the substrate binding end group are each selected from the group consisting of amine, carboxyl, and hydroxyl groups.

12. A method for adhering an implant to tissue comprising:
applying a first component comprising a biodegradable material including a tissue binding end group and a functional group selected from the group consisting of biotin and avidin to a tissue surface;
applying a second component comprising a biodegradable material including a substrate binding end group and a functional group selected from the group consisting of biotin and avidin to an implant comprising a substrate, wherein the functional group of the first component is different than the functional group of the second component; and
contacting the tissue surface with the implant to adhere the implant to the tissue via avidin-biotin affinity binding, wherein the biodegradable material of the first component, the second component, or both, is selected from the group consisting of polylactides, poly(lactic acid), polyglycolides, poly(glycolic acid), poly(trimethylene carbonate), poly(dioxanone), poly(hydroxybutyric acid), poly(hydroxyvaleric acid), poly(lactic-co-glycolic acid), poly(lactide-co-(ε-caprolactone-)), poly(glycolide-co-(ε-caprolactone)), polycarbonates, poly(pseudo amino acids), poly(amino acids), poly(hydroxyalkanoate)s, polyalkylene oxalates, polyoxaesters, polyanhydrides, polyester anyhydrides, polyortho esters, and copolymers, block copolymers, homopolymers, blends, and combinations thereof.

13. The method of claim 12, further comprising:
applying the first component to a second tissue surface; and
contacting the first and second tissue surfaces with the implant to adhere the implant to both tissue surfaces.

14. A biocompatible composition comprising:
an implant comprising a substrate;
a first component comprising a biodegradable material including a tissue binding end group and a functional group selected from the group consisting of biotin and avidin; and
a second component comprising a biodegradable material including a substrate binding end group and a functional group selected from the group consisting of biotin and avidin,
wherein the biodegradable material of the first component, the second component, or both, is selected from the group consisting of alginate, dextran, chitin, chitosan, hyaluronic acid, cellulose, collagen, gelatin, fucans, glycosaminoglycans, catgut, silk, linen, cotton, albumin, casein, zein, silk, soybean protein, and copolymers and blends thereof, and
wherein the functional group of the first component is different than the functional group of the second component and the first component adheres to a tissue surface and the second component adheres to the implant.

* * * * *